United States Patent [19]

Brown

[11] Patent Number: 5,960,403
[45] Date of Patent: Sep. 28, 1999

US005960403A

[54] HEALTH MANAGEMENT PROCESS CONTROL SYSTEM

[75] Inventor: Stephen J. Brown, San Mateo, Calif.

[73] Assignee: Health Hero Network, Mountain View, Calif.

[21] Appl. No.: 09/136,512

[22] Filed: Aug. 19, 1998

Related U.S. Application Data

[63] Continuation-in-part of application No. 08/481,925, Jun. 7, 1995, abandoned, which is a continuation-in-part of application No. 07/977,323, Nov. 17, 1992, Pat. No. 5,307,263, and a continuation-in-part of application No. 08/666,242, Jun. 20, 1996, abandoned.

[51] Int. Cl.[6] .................................................. G06F 17/40
[52] U.S. Cl. ........................ 705/2; 345/336; 395/200.38
[58] Field of Search ........................... 705/2, 3; 345/326, 345/336, 337, 338; 395/200.38, 200.39, 200.41; 600/300

[56] References Cited

U.S. PATENT DOCUMENTS

| | | | |
|---|---|---|---|
| 4,731,726 | 3/1988 | Allen, III | 364/416 |
| 4,803,625 | 2/1989 | Fu et al. | 600/483 |
| 5,016,172 | 5/1991 | Dessertine | 364/413.02 |
| 5,109,974 | 5/1992 | Beer et al. | 198/346.1 |
| 5,390,238 | 2/1995 | Kirk et al. | 379/93 |
| 5,501,231 | 3/1996 | Kaish | 128/725 |

*Primary Examiner*—Stephen R. Tkacs
*Attorney, Agent, or Firm*—Lumen Intellectual Property Services

[57] ABSTRACT

A system and method for remotely monitoring a patient and for training the patient to comply with a treatment plan for a health condition. A patient computing device collects data relating to the patient's health condition and transmits the data to a clinician computer via a communication network. The data is analyzed in the clinician computer to determine an educational need of the patient for treating the health condition. An educational program corresponding to the patient's educational need is selected and a pointer to the educational program is embedded in an electronic message to the patient. The educational program is started on the patient computing device by selecting the embedded pointer in the electronic message. As the patient works with the educational program, new data relating to the patient's health condition is collected in the patient computing device and transmitted to the clinician computer for analysis. With this continuous feedback loop between the patient and clinician, the clinician is able to monitor the patient's progress and effectively train the patient to comply with the treatment plan.

29 Claims, 15 Drawing Sheets

780

ADD/EDIT LOGBOOK ENTRY

SELECT DAY
DATE: MARCH 30, 1996 ▽

SELECT EVENT

☒ A   1 MILD WHEEZING
☐ B   2 SEVERE WHEEZING
☐ C   3 MILD COUGHING
☐ D   4 SEVERE COUGHING
         5 CHEST TIGHTNESS

ADD >>

<< REMOVE

A2 SEVERE WHEEZING

OK

CANCEL

MEDICATION

ALBUTEROL 2 PUFFS

ADD MEDICATION

NOTES

PLANNING A TRIP TO EUROPE THIS SUMMER

*FIG. 6*

HEALTH MANAGEMENT PROCESS CONTROL SYSTEM

RELATED APPLICATIONS

This is a continuation-in-part of application Ser. No. 08/481,925, filed Jun. 7, 1995, now abandoned which is a continuation-in-part of application Ser. No. 07/977,323, filed Nov. 17, 1992, and issued as U.S. Pat. No. 5,307,263. This application is also a continuation-in-part of application Ser. No. 08/666,242, filed Jun. 20, 1996, now abandoned.

BACKGROUND

1. Field of the Invention

The present invention relates to the field of health management, and in particular to a system and method for remotely monitoring a patient and for training the patient to comply with a treatment plan for a health condition.

2. Description of the Prior Art

In recent years, an increasing number of healthcare providers have initiated outpatient or home healthcare programs for their patients. The potential benefits of these home healthcare programs are particularly good for chronically ill patients, such as those suffering from asthma or diabetes, who must treat their diseases on a daily basis. However, the success of these home healthcare programs is currently limited by the ability of healthcare providers to assess, monitor and train patients to comply with treatment plans for their health conditions.

Many systems have been developed for remotely monitoring a patient's compliance with a prescribed medication plan. For example, U.S. Pat. No. 5,390,238 issued to Kirk et al. on Feb. 14, 1995 discloses a home healthcare and communication support system. The system includes a health support unit located in the patient's home for monitoring and supporting a patient. The health support unit is networked to a remote monitoring terminal for continuous remote monitoring of the patient. The health support unit includes a medication controller for measuring the patient's medicine compliance and a communications module for communicating with an operator at the monitoring terminal. The health support is further networked to the patient's healthcare provider to allow the healthcare provider access to the patient's medicine compliance data.

A similar system for monitoring a patient's medicine compliance is described in U.S. Pat. No. 5,016,172 issued to Dessertine on May 14, 1991. The system includes an automatic medicine compliance monitoring device for measuring the patient's actual medicine consumption. The monitoring device is connected to a patient computing device for recording the patient's medicine consumption. The patient computing device is further connected to a remote monitoring terminal for displaying the patient's medicine compliance to a healthcare provider. The system optionally includes a second monitoring device for monitoring a physical condition of the patient, such as heart rate, blood pressure, blood glucose, or respiration.

Although the systems described by Kirk and Dessertine allow remote monitoring of a patient's health condition and medicine compliance, they have no mechanism for ensuring patient compliance with a treatment plan. Further, these systems are not directed at providing the patient guidelines for treating a health condition. They are simply designed to monitor the patient from a remote location.

Numerous systems have also been developed for prompting a patient take prescribed doses of medication in addition to remotely monitoring the patient's health condition. For example, U.S. Pat. No. 5,501,231 issued to Kaish on Mar. 26, 1996 describes a patient-operated, hand-held system for testing and recording peak flow rates of an asthma patient. The system includes a peak flow meter for measuring the patient's peak flow rates and an alarm for prompting the patient to take a prescribed dose of medication. In using the system, the patient records his or her peak flow rates over a predetermined period of time, typically fifteen days to six months, before returning the system to a doctor for recovery of the peak flow data. At this time, the doctor may optionally reprogram the system with new alarm times and prescribed medicine doses.

Although the system described by Kaish has the advantage of prompting a patient to take medication, it lacks any mechanism for training the patient to actually comply with the prompts. The system is limited to issuing preprogrammed medicine instructions to the patient without teaching the patient why or how to follow the instructions. Further, the system cannot identify any problems the patient is experiencing in following a treatment plan for his or her health condition or teach the patient how to solve the problems. As a result, the patient may not be able to comply with the prescribed treatment plan, severely limiting the effectiveness of this home healthcare system. Additionally, the system described by Kaish does not permit continuous feedback between the doctor and patient for ongoing adjustment of the treatment plan.

Another system for remotely monitoring a patient and for prompting a patient to take a prescribed dose of medication is disclosed in U.S. Pat. No. 4,731,726 issued to Allen on Mar. 15, 1988. Allen describes a diabetes management system having a blood glucose meter for measuring a patient's blood glucose levels and for sending the blood glucose measurements to a physician. The system further includes a user interface for entering in the system data relating to the patient's medication usage, exercise routine, and dietary intake. Based on the entered data, the system calculates a recommended insulin dose for the patient using a physician prescribed algorithm stored in its memory.

Allen's system suffers from the same disadvantage as Kaish's system in failing to train the patient to comply with the prescribed treatment plan. The system is limited to issuing dosage instructions based on a preprogrammed algorithm without identifying any problems the patient is experiencing with the diabetes program or teaching the patient how to solve the problems. Consequently, the effectiveness of this diabetes management system is also limited.

A similar system for home management of diabetes is disclosed in U.S. Pat. No. 5,109,974 issued to Beckers on May 28, 1991. The system includes a physician computer for developing a diabetes therapy program and a patient recorder having an interface for exchanging data with the physician computer. The recorder has a blood glucose test strip for measuring the patient's blood glucose levels and a user interface for entering in the recorder data relating to the patient's insulin usage, exercise routines, and dietary intake. Using the patient data and therapy guidelines downloaded from the physician computer, the recorder calculates and displays to the patient a recommended insulin dosage, exercise plan, and diet. The recorder also receives from the physician computer new therapy guidelines developed from the patient's recorded data.

Although the diabetes management program disclosed by Beckers has the advantage of adjusting a patient's recommended therapy program based on remote monitoring of the patient, it also has the same disadvantage as the previous systems in failing to teach the patient how to follow the prescribed treatment plan. Becker's system has no mechanism for identifying problems the patient is experiencing with the diabetes program or for teaching the patient how to solve the problems. As a result, Becker's system is also ineffective for training the patient to comply with the diabetes treatment plan.

OBJECTS AND ADVANTAGES OF THE INVENTION

In view of the above, it is an object of the present invention to provide a system and method for remotely monitoring a patient and for effectively training the patient to comply with a treatment plan for a health condition. It is another object of the invention to provide a method for teaching a patient to solve a specific problem the patient is experiencing with a treatment plan. A further object of the invention is to provide a system that allows continuous feedback between a clinician and patient for ongoing adjustment of a treatment plan.

The invention provides a new and useful system for healthcare monitoring and patient training based on a small microprocessor-based unit or a personal computer which is networked with the clinician's resources and requisite databases.

These and other objects and advantages will become more apparent after consideration of the ensuing description and the accompanying drawings.

SUMMARY OF THE INVENTION

The invention presents a system and method for remotely monitoring a patient and for training the patient to comply with a treatment plan for a health condition. The system includes a patient computing device, such as a personal computer or network terminal, for collecting data relating to the health condition. In the preferred embodiment, the data includes measurements of a physical characteristic of the health condition, such as blood glucose measurements for a diabetic patient or peak flow measurements for an asthmatic patient. Also in the preferred embodiment, the data includes measurements of a psychological characteristic of the health condition, such as the patient's knowledge, comprehension, or attitude in treating the health condition.

The system further includes a clinician computer having a data analysis program for analyzing the data to determine an educational need of the patient. The clinician computer also has a message program, such as an electronic mail program, for composing an electronic message to the patient. The electronic message contains a pointer to an educational program corresponding to the patient's educational need. The pointer is a prompt embedded in the message. When the patient selects the pointer the latter loads and executes the educational program instructions linked to the message. A communication network connects the patient computing device and the clinician computer and transmits the data and the electronic message therebetween.

A preferred method of using the system includes the steps of entering data relating to the patient's health condition into the patient computing device and transmitting the data from the patient computing device to the clinician computer via the communication network. The method further includes the steps of analyzing the data received in the clinician computer to determine an educational need of the patient and selecting an educational program corresponding to the educational need. A pointer to the selected educational program is then embedded in an electronic message to the patient. The electronic message is transmitted through the communication network from the clinician computer to the patient computing device.

The educational program is started on the patient computing device when the patient selects the embedded pointer in the electronic message. As the patient works with the educational program, new data relating to the patient's health condition is collected in the patient computing device and transmitted to the clinician computer for analysis. With this continuos feedback loop between the patient and clinician, the clinician is able to monitor the patient's progress and effectively train the patient to comply with the treatment plan.

BRIEF DESCRIPTION OF THE DRAWINGS

FIGS. 5–6 are sample logbook entry screens appearing on the patient computing device of FIG. 4.

DESCRIPTION

Figure 1A:
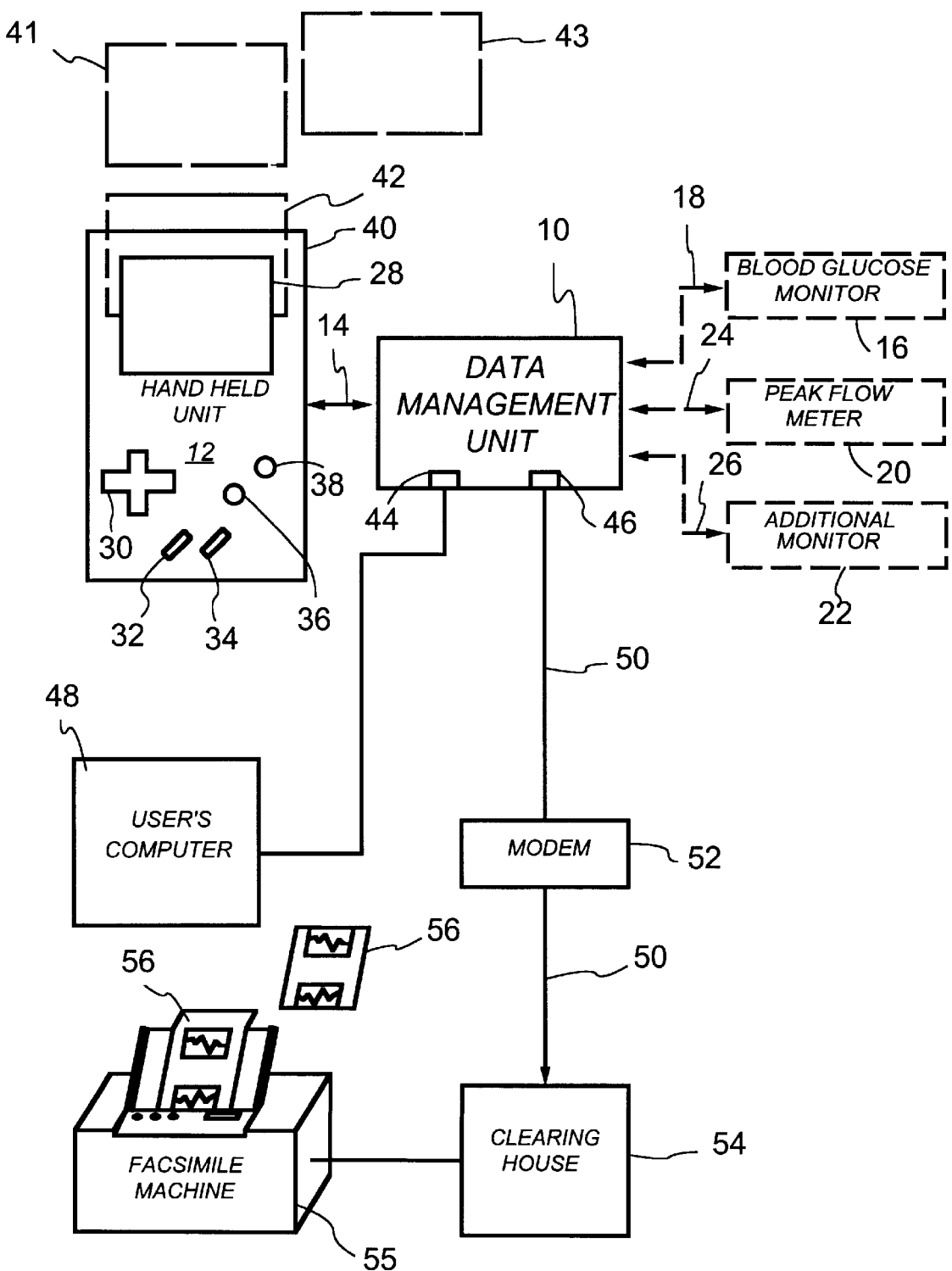
FIG. 1A is a block diagram that illustrates a healthcare monitoring system arranged in accordance with the invention.

FIG. 1A depicts a self-care health monitoring system arranged in accordance with the invention. In the arrangement shown in FIG. 1A, a data management unit 10 is electrically interconnected with a computing device such as a computer or a handheld microprocessor-based unit 12 via a cable 14. In the depicted arrangement, data management unit 10 also is electrically interconnected with a blood glucose monitor 16 of the type capable of sensing blood glucose level and producing an electrical signal representative thereof.

Although FIG. 1A illustrates blood glucose monitor 16 as being connected to data management unit 10 by a cable 18, it may be preferable to construct blood glucose monitor 16 as a plug-in unit that is placed in a recess or other suitable opening or slot in data management unit 10.

Also shown in FIG. 1A are two additional monitoring devices 20 and 22, which are electrically connected for serial data communication with data management unit 10 via cables 24 and 26, respectively. Monitoring units 20 and 22 of FIG. 1A represent devices other than blood glucose monitor 16 that can be used to configure the invention for self-care health monitoring applications other than (or in addition to) diabetes care. For example, as is indicated in FIG. 1A, the monitoring device 20 can be a peak-flow meter that provides a digital signal representative of the airflow that results when a person suffering from asthma or another chronic respiratory affliction expels a breath of air through the meter. As is indicated by monitor 22 various other devices can be provided for monitoring conditions such as blood pressure, pulse, and body temperature to thereby realize systems for self-care monitoring and control of conditions such as hypertension, certain heart conditions and various other afflictions and physical conditions. Upon understanding the hereinafter discussed aspects and features of the invention it will be recognized that the invention is easily implemented for these and other types of healthcare monitoring.

As is shown in FIG. 1A, handheld microprocessor unit 12 includes a display screen 28 and a plurality of switches or keys (30, 32, 34, 36, and 38), which are mounted on a housing 40. Located in the interior of housing 40, but not shown in FIG. 1A, are a microprocessor, memory circuits, and circuitry that interfaces switches 30, 32, 34, 36 and 38 with the microprocessor.

Stored in the memory of program microprocessor unit 12 is a set of program instructions that establishes a data protocol that allows microprocessor unit 12 to perform digital data signal processing and generate desired data or graphics for display on display unit 28 when a program cartridge 42 is inserted in a slot or other receptacle in housing 40. That is, program cartridge 42 includes read-only memory units (or other memory means such as battery-powered random access memory) which store program instructions and data that adapt handheld microprocessor 12 for operation in a blood glucose monitoring system. More specifically, when the instructions and data of program cartridge 42 are combined with program instructions and data included in the internal memory circuits of microprocessor unit 12, microprocessor unit 12 is programmed for processing and displaying blood glucose information in the manner described below and additional monitors 22 to provide health monitoring for asthma and various other previously mentioned chronic conditions. In each case, the plurality of switches or keys 30, 32, 34, 36, and 38 are selectively operated to provide signals that result in pictorial and/or alphanumeric information being displayed by display unit 42.

Various devices are known that meet the above-set forth description of microprocessor unit 12. For example, compact devices are available in which the plurality of keys allows alphanumeric entry and internal memory is provided for storing information such as names, addresses, phone numbers, and an appointment calendar. Small program cartridges or cards can be inserted in these devices to program the device for various purposes such as the playing of games. More recently, less compact products that have more extensive computational capability and are generally called "palm top computers" have been introduced into the marketplace. These devices also can include provision for programming the device by means of an insertable program card or cartridge. Alternatively, the program can be loaded into their memory from a network or via a modem connection. A person of average skill in the art will appreciate that there exist other suitable methods for loading programs into suitable computer devices.

Another advantage of realizing handheld microprocessor unit 12 in the form of a compact video game system is the relatively simple, yet versatile arrangement of switches that is provided by such a device. For example, a compact video game system includes a control pad 30 that allows an object displayed on display unit 42 to be moved in a selected direction (i.e., up-down or left-right). As also is indicated in FIG. 1A, compact video game systems typically provide two pair of distinctly-shaped push button switches. A pair of spaced-apart circular push button switches (36 and 38) and a pair of elongate switches (32 and 34) are provided. The functions performed by the two pairs of switches is dependent upon the program instructions contained in each program cartridge 42.

Yet another advantage of utilizing a compact video game system for handheld microprocessor-based unit 12 of FIG. 1A is the widespread popularity and low cost of such units. In this regard, manufacture and sale of a data management unit 10, blood glucose monitor 16 and program cartridge 42 that operate in conjunction with a compact microprocessor-based video allows the self-care health monitoring system of FIG. 1A to be manufactured and sold at a lower cost than could be realized in an arrangement in which handheld unit 12 is designed and manufactured solely for use in the system.

An even further advantage of using a compact video game system for handheld microprocessor 12 is that such video game systems include means for easily establishing the electrical interconnection provided by cable 14. In particular, such compact video game systems include a connector 40 mounted to the game unit housing and a cable that can be connected between the connectors of two video game units to allow interactive operation of the two interconnected units (i.e., to allow contemporaneous game play by two players or competition between players as they individually play identical but separate games). The cable supplied with handheld microprocessor unit 12 can be used as cable 14 to establish serial data communication between the handheld microprocessor unit 12 (compact video game system) and data management unit 10.

Depending upon the operational mode selected by the user, data is supplied to data management unit 10 by blood glucose monitor 16, by additional monitors (20 and 22 in FIG. 1A) or any interconnected computers or data processing facility (such as the hereinafter described user's computer 48 and clearinghouse 54). During such operation, mode switches 30, 32, 34, 36 and 38 are selectively activated so that signals are selectively coupled to microprocessor unit 12 and processed in accordance with program instructions stored in program cartridge 42. The signal processing performed by microprocessor unit 12 results in the display of alphanumeric, symbolic, or graphic information on the video game display 28, which allow the user to control system operation and obtain desired test results and other information.

Although the above-discussed advantages apply to use of the invention by all age groups, employing a compact video game system in the practice of the invention is of special significance in monitoring a child's blood glucose or other health parameters. Children and young adults are familiar with compact video game systems. Thus, children will accept a health monitoring system incorporating a compact video game system more readily than a traditional system, even an embodiment of the invention that uses a different type of handheld microprocessor unit. Moreover, an embodiment of the invention that functions in conjunction with a compact video game system can be arranged to motivate children to monitor themselves more closely than they might otherwise by incorporating game-like features and/or animation in system instruction and test result displays. Similarly, the program instructions can be included in program cartridges 41, 42 and 43 (or additional cartridges) that allow children to select game-like displays that help educate the child about his or her condition and the need for monitoring.

With continued reference to FIG. 1A, data management unit 10 includes a data port 44 that allows communication between data management unit 10 and a personal computer 48 (or other programmable data processor). Data port 44 is, for example, an RS-232 connection that allows serial data communication between data management unit 10 and persona: computer 48. In the practice of the invention, personal computer 48 can be used to supplement data management unit 10 by, for example, performing more complex analyses of blood glucose and other data that has been supplied to and stored in the memory circuits of data management unit 10. with respect to embodiments of the invention configured for use by a child, personal computer 48 can be used by a parent or guardian to review and analyze the child's progress and to produce printed records for subsequent review by a healthcare professional.

Alternatively, personal computer 48 can be used to supply data to data management unit 10 that is not conveniently supplied by using handheld microprocessor switches 30, 32, 34, 36 and 38 as an operator interface to the system of FIG. 1A. For example, some embodiments of the invention may employ a substantial amount of alphanumeric information that must be entered by the system user. Although it is possible to enter such data by using switches 30, 32, 34, 36 and 38 in conjunction with menus and selection screens displayed on display screen 28 of FIG. 1A, it may be more advantageous to use a device such as personal computer 48 for entry of such data. However, if personal computer 48 is used in this manner, some trade-off of system features may be required because data management unit 10 must be temporarily interconnected with personal computer 48 during these operations. That is, some loss of system mobility might result because a suitably programmed personal computer would be needed at each location at which data entry or analysis is to occur. Of course, it will be recognized by a person of average skill in the art that in certain embodiments personal computer 48 can absorb the entire functionality of unit 12 and data management unit 10. A system based on computer 48 only may be more successful with adult patients or when the data to be displayed is very complicated and requires the entire computer screen.

As is indicated in FIG. 1A, data management unit 10 of the currently preferred embodiments of the invention also includes a modem that allows data communication between data management unit 10 and an information service, computing facility or clearinghouse 54 via a conventional telephone line 50 in and a modem 52 that interconnects clearinghouse 54 via telephone line 50.

Clearinghouse 54 facilitates communication between a user of the system and his or her healthcare professional and can provide additional services such as updating system software or downloading specific programs to the user. In fact, in one embodiment clearing house 54 is the computer used by the clinician. As is indicated by facsimile machine 55 of FIG. 1A, a primary function of clearinghouse 54 is providing the healthcare professional with standardized reports 56, which indicate both the current condition and condition trends of the system user. Although a single facsimile machine 55 is shown in FIG. 1A, it will be recognized that numerous healthcare professionals (and hence facsimile machine 55) can be connected in signal communication with a clearinghouse 54. In this situation each healthcare professional may have his or her own clinician computer linked to clearinghouse 54 according to methods well known in the art.

Regardless of whether a compact video game system, another type of commercially available handheld microprocessor-based unit, or a specially designed unit is used, the system of FIG. 1A provides a self-care blood glucose monitoring system in which program cartridge 42: (a) adapts handheld microprocessor unit 12 for displaying instructions for performing the blood glucose test sequence and associated calibration and test procedures; (b) adapts handheld microprocessor unit 12 for displaying (graphically or alphanumerically) statistical data such as blood glucose test results taken during a specific period of time (e.g., a day, week, etc.); (c) adapts handheld microprocessor unit 12 for supplying control signals and signals representative of food intake or other useful information to data management unit 10; (d) adapts handheld microprocessor unit 12 for simultaneous graphical display of blood glucose levels with information such as food intake; and, (e) adapts handheld microprocessor unit 12 for displaying information or instructions from a healthcare professional that are coupled to data management unit 10 from a clearinghouse 54. In the event that computer 48 absorbs all of the functions of unit 12 and data management unit 10, cartridge 42 or appropriate software is communicated directly to computer 48 instead. Computer 48 then performs all of the above functions. The manner in which the arrangement of FIG. 1A implements the above-mentioned functions and others can be better understood with reference to FIG. 2 discussed further below.

Figure 1B:
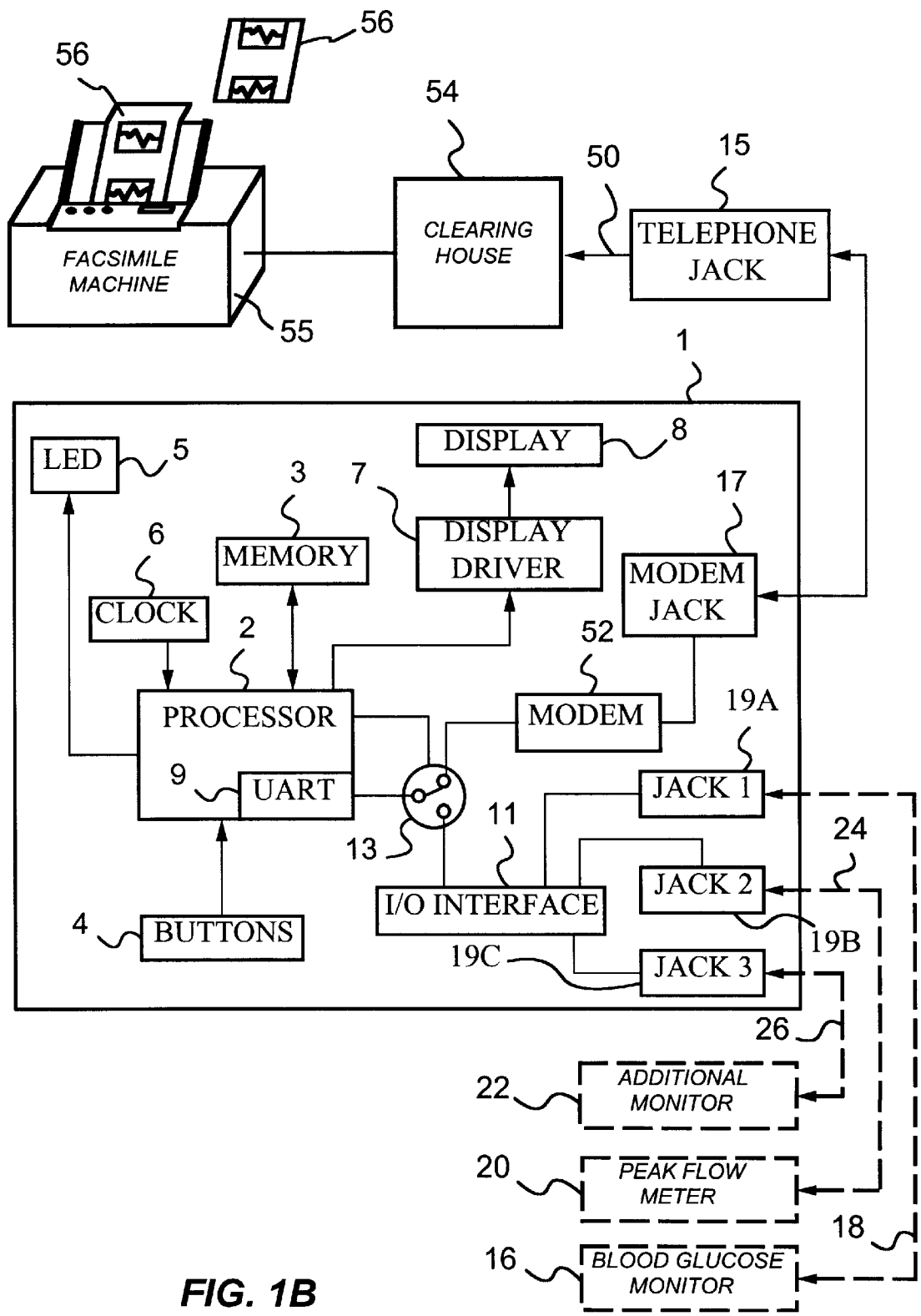
FIG. 1B is a schematic block diagram illustrating an alternative healthcare monitoring system arranged in accordance with the invention.

Alternatively, the functionality of handheld unit 12, computer 48, data management unit 10 and modem 52 can be replaced by a single integrated device. Such an embodiment is shown in FIG. 1B, by a schematic block diagram of an integrated device 1. Device 1 includes a microprocessor 2 and a memory 3 connected to microprocessor 2. Memory 3 is preferably a non-volatile memory, such as a serial EEPROM. Memory 3 stores programs or script programs received from clearing house 54, measurements received from monitoring devices 16, 20 or 22, and the patient's responses. Microprocessor 2 also includes built-in read only memory (ROM) which stores firmware for controlling the operation of apparatus 1. The firmware includes a script interpreter used by microprocessor 2 to execute the script programs. The script interpreter interprets script commands which are executed by microprocessor 2. Specific techniques for interpreting and executing script commands in this manner are well known in the art.

Microprocessor 2 is preferably connected to memory 3 using a standard two-wire $I^2C$ interface. Microprocessor 2 is also connected to user input buttons 4, LED 5, a clock 6, and a display driver 7. Clock 6 indicates the current date and time to microprocessor 2. For clarity of illustration, clock 6 is shown as a separate component, but is preferably built into microprocessor 2. Display driver 7 operates under the control of microprocessor 2 to display information on display 8. Microprocessor 2 is preferably a PIC 16C65 processor which includes a universal asynchronous receiver transmitter (UART) 9. UART 9 is for communicating with modem 52 and a device interface 11. A CMOS switch 13 under the control of microprocessor 2 alternately connects modem 52 and interface 11 to UART 9.

Modem 52 is connected to a telephone jack 15 through modem jack 17. Modem 52 is for exchanging data with clearing house 54 through telephone line or any other suitable communication network 50. The data includes programs, e.g., script programs which are received from the server as well as responses to queries, device measurements, any required script identification codes, and the patient's unique identification code which modem 52 transmits to the clearing house. Modem 52 is preferably a complete 28.8 K modem commercially available from Cermetek, although any suitable modem may be used.

Device interface 11 is connected to device jacks 19A, 19B, and 19C. Device interface 11 is for interfacing with monitoring devices 16, 20, 22 which can include blood glucose meters, respiratory flow meters, blood pressure cuffs, weight scales, pulse rate monitors or any other suitable patient monitoring devices. Device interface 11 operates under the control of microprocessor 2 to collect measurements from the monitoring devices and to output the measurements to microprocessor 2 for storage in memory 3. In the preferred embodiment, interface 11 is a standard RS232 interface. In alternative embodiments, apparatus 1 may include multiple device interfaces to accommodate monitoring devices which have different connection standards.

Figure 2:
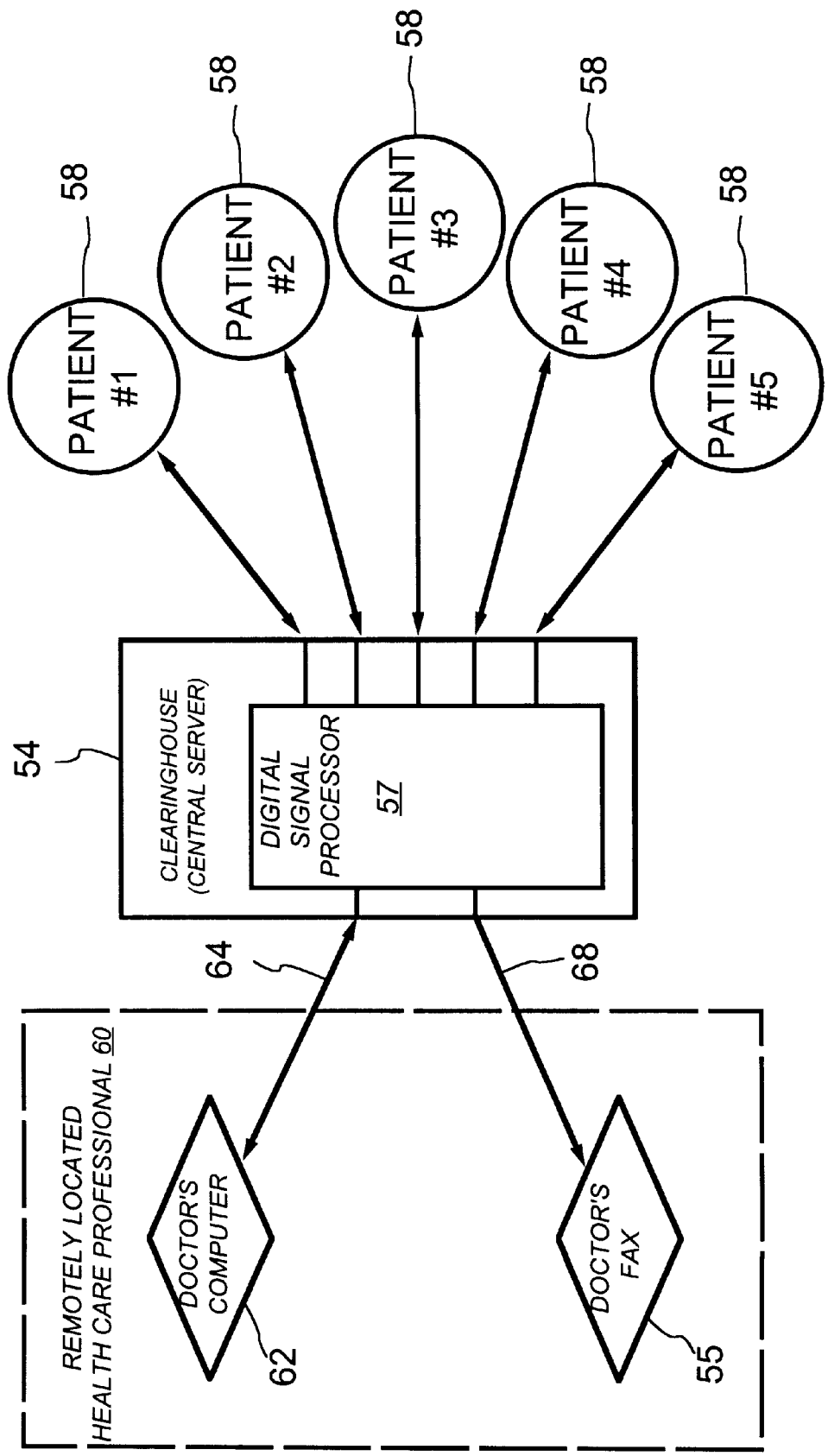
FIG. 2 diagrammatically illustrates monitoring systems constructed in accordance with the invention connected in signal communication with a remotely located computing facility which includes provision for making the data supplied by the monitoring system of the invention available to a designated healthcare professional and/or for providing data and instructions to the system user.

As shown in FIG. 2, clearinghouse 54 receives data from a plurality of self-care microprocessor-based healthcare systems of the type shown in either FIG. 1A or FIG. 1B, with the individual self-care health monitoring systems being indicated in FIG. 2 by reference numeral 58. Preferably, the data supplied to clearinghouse 54 by each individual self-care health monitoring system 58 consists of "raw data," i.e., test results and related data that was stored in memory circuits of data management unit 10, without further processing by data management unit 10. For example, with respect to the arrangement shown in FIG. 1A or FIG. 1B, blood glucose test results and associated data such as food intake information, medication dosage and other such conditions are transmitted to clearinghouse 54 and stored with a digitally encoded signal that identifies both the source of the information (i.e., the system user or patient) and those having access to the stored information (i.e., the system user's doctor or other healthcare professional).

As shall be recognized upon understanding the manner in which it operates, clearinghouse 54 can be considered to be a central server for the various system users 58 and each healthcare professional 60. Thus, clearinghouse 54 includes conventionally arranged and interconnected digital processing equipment, i.e., digital signal processor 57 which receives digitally encoded information from user 58 or healthcare professional 60; processes the information as required; stores the information (processed or unprocessed) in memory if necessary; and transmits the information to an intended recipient (i.e., user 58 or healthcare professional 60).

In FIG. 2, rectangular outline 60 represents one of numerous remotely located healthcare professionals who can utilize clearinghouse 54 and the arrangement described relative to FIG. 1A or FIG. 1B in monitoring and controlling patient healthcare programs. Shown within outline 60 is a computer 62 (e.g., personal computer), which is coupled to clearinghouse 54 by means of a modem (not shown in FIG. 2) and a telephone line 64. Also shown in FIG. 2 is the previously mentioned facsimile machine 55, which is coupled to clearinghouse 54 by means of a second telephone line 68. Using the interface unit of computer 62 (e.g., a keyboard or pointing device such as a mouse), the healthcare professional can establish data communication between computer 62 and clearinghouse 54 via telephone line 64. Once data communication is established between computer 62 and clearinghouse 54, patient information can be obtained from clearinghouse 54 in a manner similar to the manner in which subscribers to various database services access and obtain information.

In particular, the healthcare professional can transmit an authorization code to clearinghouse 54 that identifies the healthcare professional as an authorized user of the clearinghouse and, in addition, can transmit a signal representing the patient for which healthcare information is being sought. As is the case with conventional database services and other arrangements, the identifying data is keyed into computer 62 by means of a conventional keyboard (not shown in FIG. 2) in response to prompts that are generated at clearinghouse 54 for display by the display unit of computer 62 (not shown in FIG. 2).

Depending upon the hardware and software arrangement of clearinghouse 54 and selections made by the healthcare professional via computer 62, patient information can be provided to the healthcare professional in different ways. For example, computer 62 can be operated to access data in the form that it is stored in the memory circuits of clearinghouse 54 (i.e., raw data that has not been processed or altered by the computational or data processing arrangements of clearinghouse 54). Such data can be processed, analyzed, printed and/or displayed by computer 62 using commercially available or custom software. On the other hand, various types of analyses may be performed by clearinghouse 54 with the results of the analyses being transmitted to the remotely located healthcare professional 60. For example, clearinghouse 54 can process and analyze data in a manner identical to the processing and analysis provided by the self-care monitoring system of FIG. 1A or FIG. 1B. With respect to such processing and any other analysis and processing provided by clearinghouse 54, results expressed in alphanumeric format can be sent to computer 62 via telephone line 64 and the modem associated with computer 62, with conventional techniques being used for displaying and/or printing the alphanumeric material for subsequent reference.

The arrangement of FIG. 2 also allows the healthcare professional to send messages and/or instructions to each patient via computer 62, telephone line 64, and clearinghouse 54. In particular, clearinghouse 54 can be programmed to generate a menu that is displayed by computer 62 and allows the healthcare professional to select a mode of operation in which information is to be sent to clearinghouse 54 for subsequent transmission to a user of the system described relative to FIG. 1A or FIG. 1B. This same menu (or related submenus) can be used by the healthcare professional to select one or more modes of operation of the above-described type in which either unmodified patient data or the results of data that has been analyzed by clearinghouse 54 is provided to the healthcare provider via computer 62 and/or facsimile machine 55.

Operation of the arrangement of FIG. 2 to provide the user of the invention with messages or instructions such as changes in medication or other aspects of the healthcare program, e.g., instructional programs, is similar to the operation that allows the healthcare professional to access data sent by a patient, i.e., transmitted to clearinghouse 54 by a data management unit 10 of FIG. 1A or FIG. 1B. The process differs in that the healthcare professional enters the desired message or instruction via the keyboard or other interface unit of computer 62. Once the data is entered and transmitted to clearinghouse 54, it is stored for subsequent transmission to the user for whom the information or instruction is intended.

With respect to transmitting stored messages or instructions to a user of the invention, at least two techniques are available. The first technique is based upon the manner in which operational modes are selected in the practice of the invention. Specifically, in the currently preferred embodiments of the invention, program instructions that are stored in data management unit 10 and program cartridge 42 cause the system of FIG. 1A or FIG. 1B to generate menu screens which are displayed by display unit 28 of microprocessor unit 12. The menu screens allow the system user to select the basic mode in which the system is to operate and, in addition, allow the user to select operational subcategories within the selected mode of operation. Various techniques are known to those skilled in the art for displaying and selecting menu items. For example, in the practice of this invention, one or more main menus can be generated and displayed which allow the system user to select operational modes that may include: (a) a monitor mode (e.g., monitoring of blood glucose level); (b) a display mode (e.g., displaying previously obtained blood glucose test results or other relevant information); (c) an input mode (e.g., a mode for entering data such as providing information that relates to the healthcare regimen, medication dosage, food intake, etc.); and, (d) a communications mode (for establishing a communication link between data management unit 10 and personal computer 48 of FIG. 1A or FIG. 1B; or between data management unit 10 and a remote computing facility such as clearinghouse 54 of FIG. 2).

In embodiments of the invention that employ a compact video game system for handheld microprocessor unit 12, the selection of menu screens and the selection of menu screen items preferably is accomplished in substantially the same manner as menu screens and menu items are selected during the playing of a video game. For example, the program instructions stored in data management unit 10 and program cartridge 42 of the arrangement of FIG. 1A or FIG. 1B can be established so that a predetermined one of the compact video game switches (e.g., switch 32) allows the system user to select a desired main menu in the event that multiple main menus are employed. When the desired main menu is displayed, operation by the user of control pad 30 allows a cursor or other indicator that is displayed on the menu to be positioned adjacent to or over the menu item to be selected. Activation of a switch (e.g., switch 36 of the depicted handheld microprocessor unit 12) causes the handheld microprocessor unit 12 and/or data management unit 10 to initiate the selected operational mode or, if selection of operational submodes is required, causes handheld microprocessor unit 12 to display a submenu.

In view of the above-described manner in which menus and submenus are selected and displayed, it can be recognized that the arrangement of FIG. 1A or FIG. 1B can be configured and arranged to display a menu or submenu item that allows the user to obtain and display messages or instructions that have been provided by a healthcare professional and stored in clearinghouse 54. For example, a submenu that is generated upon selection of the previously mentioned communications mode can include submenu items that allow the user to select various communication modes, including a mode in which serial data communication is established between data management unit 10 and clearinghouse 54 and data management unit 10 transmits a message status request to clearinghouse 54. When this technique is used, the data processing system of clearinghouse 54 is programmed to search the clearinghouse memory to determine whether a message exists for the user making the request. Any messages stored in memory for that user are then transmitted to the user and processed for display on display unit 28 of handheld microprocessor unit 12. Of course, the message may include an entire program, e.g., an instructional video. If no messages exist, clearinghouse 54 transmits a signal that causes display unit 28 to indicate "no messages." In this arrangement, clearinghouse 54 preferably is programmed to store a signal indicating that a stored message has been transmitted to the intended recipient (user). Storing such a signal allows the healthcare professional to determine that messages sent to clearinghouse 54 for forwarding to a patient have been transmitted to that patient.

In addition, the program instructions stored in data management unit 10 preferably allow the system user to designate whether received messages and instructions are to be stored in the memory of data management unit 10 for subsequent retrieval or review. In addition, in some instances it may be desirable to program clearinghouse 54 and data management unit 10 so that the healthcare professional can designate (i.e., flag) information such as changes in medication that will be prominently displayed to the user (e.g., accompanied by a blinking indicator) and stored in the memory of data management unit 10 regardless of whether the system user designates the information for storage.

A second technique that can be used for forwarding messages or instructions to a user does not require the system user to select a menu item requesting transmission by clearinghouse 54 of messages that have been stored for forwarding to that user. In particular, clearinghouse 54 can be programmed to operate in a manner that either automatically transmits stored messages for that user when the user operates the system of FIG. 1A or FIG. 1B to send information to the clearinghouse or programmed to operate in a manner that informs the user that messages are available and allows the user to access the messages when he or she chooses to do so.

Practicing the invention in an environment in which the healthcare professional uses personal computer in some or all of the above-discussed ways can be very advantageous. On the other hand, the invention also provides healthcare professionals timely information about system users without the need for a computer (62 in FIG. 2) or any equipment other than a conventional facsimile machine 55 in FIGS. 1 and 2. Specifically, information provided to clearinghouse 54 by a system user 58 can be sent to a healthcare professional 60 via telephone line 68 and facsimile machine 55, with the information being formatted as a standardized graphic or textual report 56. Formatting a standardized report 56 (i.e., analyzing and processing data supplied by blood glucose monitor 16 or other system monitor or sensor) can be effected either by data management unit 10 or within the clearinghouse facility 54.

A preferred embodiment of the invention is focused on sending the patient an educational program corresponding to an educational need as assessed by the system of the invention. The adaptation of the system of FIGS. 1 and 2 for this purpose is shown in detail in FIGS. 3–15.

Figure 3:
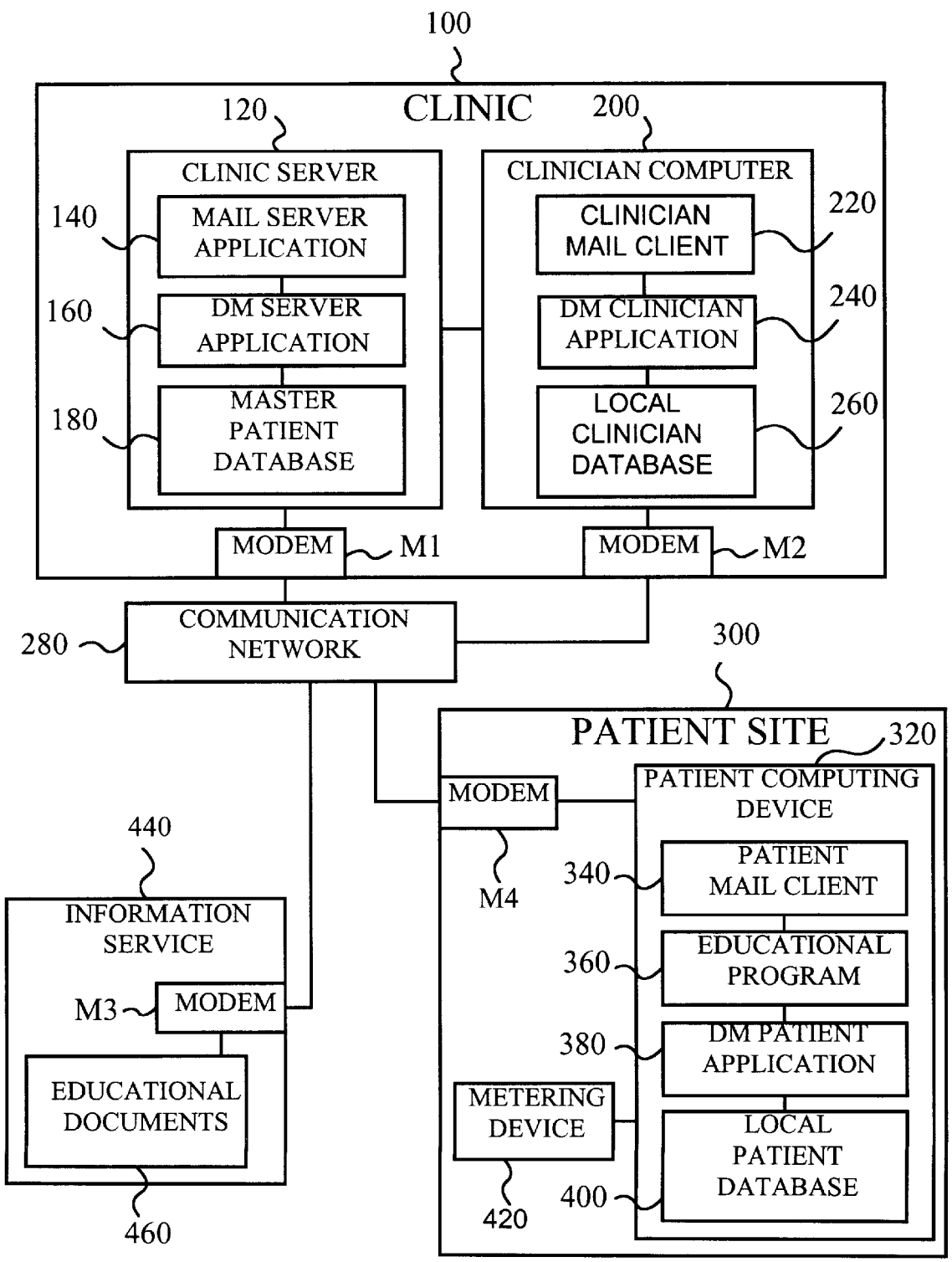
FIG. 3 is a schematic block diagram of the main components of a health management process control system according to the invention.

FIG. 3 shows the main components of a health management system for remotely monitoring a patient and for training the patient to comply with a treatment plan for a health condition. A healthcare clinic 100 has a clinic server computer 120 that includes a mail server application 140 for managing electronic mail services for clinic 100. Clinic server 120 also includes a master patient database 180 for storing data relating to each patient managed by clinic 100. Clinic server 120 further includes a data management server application 160 for managing and performing database operations taking place on master patient database 180. Clinic server 120 is coupled to a modem M1 for connecting server 120 to a communication network 280.

A clinician computer 200 is networked to clinic server 120. Clinician computer 200 has a clinician mail client application 220 for composing, sending, and receiving electronic mail messages. Clinician computer 200 further includes a local clinician database 260 for storing patient data downloaded from clinic server 120. Clinician computer 200 also has a clinician data management application 240 for managing patient data stored in local clinician database 260. Clinician computer 200 is coupled to a modem M2 for connecting clinician computer 200 to communication network 280.

A patient computing device 320 for collecting patient data relating to the patient's health condition is located at a patient site 300, typically the patient's home. In the preferred embodiment, patient computing device 320 is a personal computer having a display monitor. However, in alternative embodiments, patient computing device 320 may be any information processing and display unit, such as a network terminal, a television set with a set-top cable converter box, a personal digital assistant, or a video educational program system as described above.

Patient computing device 320 includes a patient mail client 340 for sending and receiving electronic mail messages. Patient computing device 320 further includes a local patient database 400 for storing the patient data and a data management application 380 for managing the patient data stored in database 400. Patient computing device 320 is coupled to a modem M4 for connecting patient computing device 320 to communication network 280.

A metering device 420 is connected to patient computing device 320. Device 420 is for measuring a physical characteristic of the patient's health condition, such as blood glucose levels for a diabetic patient or peak flow rates for an asthmatic patient, and for uploading the measurements to computer 320. Specific techniques for connecting a metering device to a patient computing device for remote monitoring of a patient are well known in the art.

An on-line information service 440 having educational documents 460 is connected to communication network 280 through a modem M4. In the preferred embodiment, on-line information service 440 is a world wide web service having educational documents 460 located on a world wide web site, such as the American Diabetes Association's web site or the American Lung Association's web site. Of course, there are many other on-line services such as Compuserve, America On-Line, and other electronically accessible database servers that may be used as a source of educational documents in alternative embodiments.

An educational video educational program 360 for training the patient to comply with a treatment plan for his or her health condition is installed on patient computing device 320. In the preferred embodiment, educational video educational program 360 is a Health Hero® video educational program, such as Packy & Marlon®, commercially available from Health Hero Network, Inc. of Mountain View, Calif. Educational video educational program 360 is preferably a role-playing educational program that permits a patient to simulate treating his or her health condition. Educational program 360 is further capable of scoring patient responses to the role-playing program to determine the patient's knowledge, comprehension, and attitude in complying with the treatment plan for his or her health condition.

For example, in the educational video educational program Packy & Marlon®, one or two players manage the diabetes of two educational program characters and attempt to progress to higher educational program levels through successful management of the diabetes. Diabetes management steps in the educational program include selecting appropriate foods, taking insulin doses, measuring blood glucose levels, and answering questions about diabetes. Educational program responses are recorded in several categories to indicate the player's knowledge, comprehension, and attitude in managing diabetes. A player's attitude may also be determined by recording whether the player played alone or with a friend, indicating if the player is adjusting socially to his or her health condition.

Figure 4:
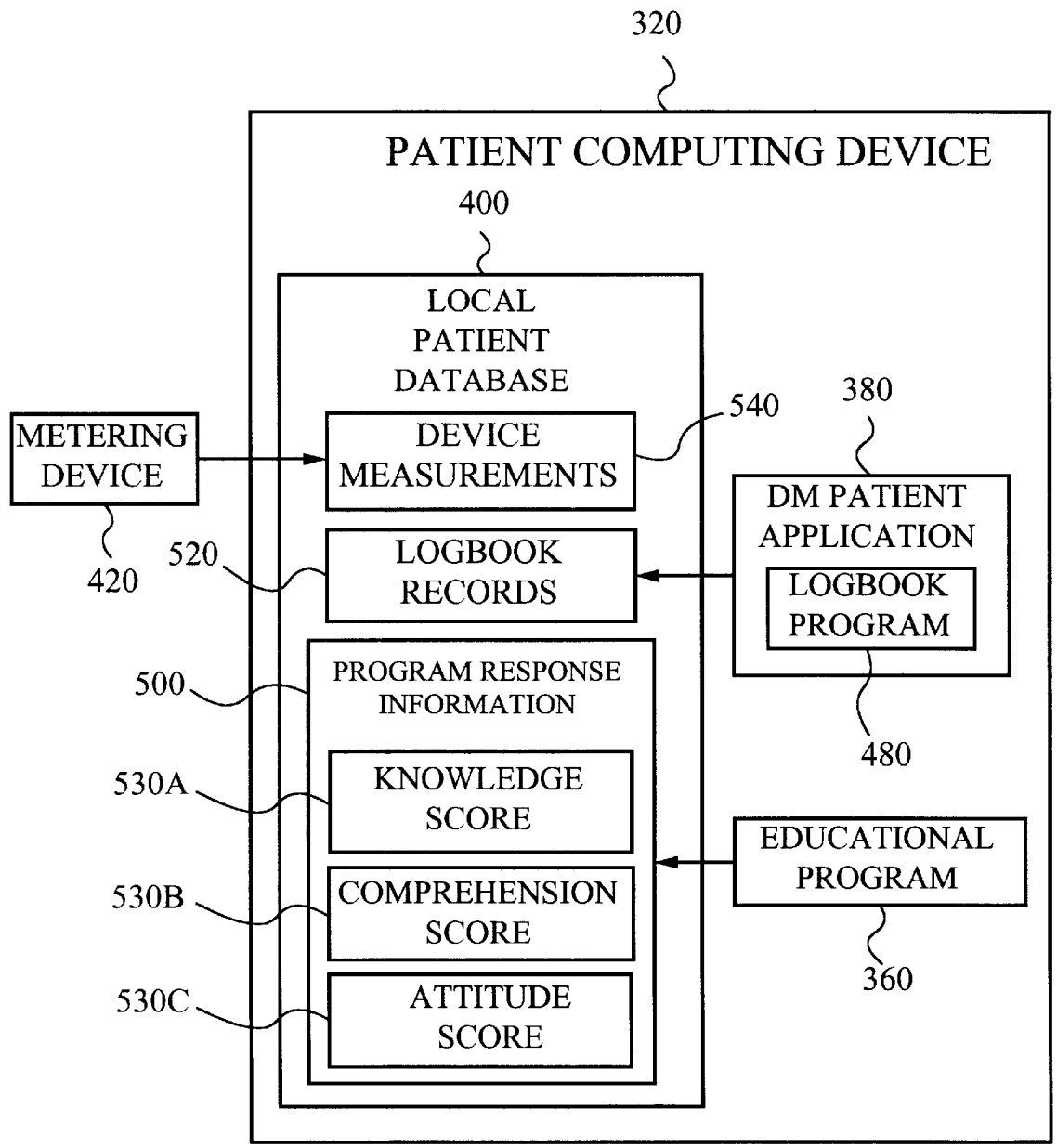
FIG. 4 is a schematic block diagram illustrating the entering of patient data into a patient computing device according to the method of the invention.

FIG. 4 is a schematic block diagram illustrating the entering of patient data relating to the patient's health condition into local patient database 400. The patient data includes educational program response information 500 derived by scoring patient responses to educational video educational program 360. Educational program response information 500 includes a knowledge score 530A for indicating the patient's understanding of the treatment plan. Educational program response information 500 also includes a comprehension score 530B for indicating a cognitive ability of the patient to understand an educational program designed to teach compliance with the treatment plan. Educational program response information 500 further includes an attitude score 530C for indicating the patient's attitude toward complying with the treatment plan. The patient data further includes device measurements 540 received from metering device 420 and logbook records 520 of the patient's treatment plan. Logbook records 520 are entered into database 400 using a logbook program 480 included in patient data management application 380.

Figure 5:
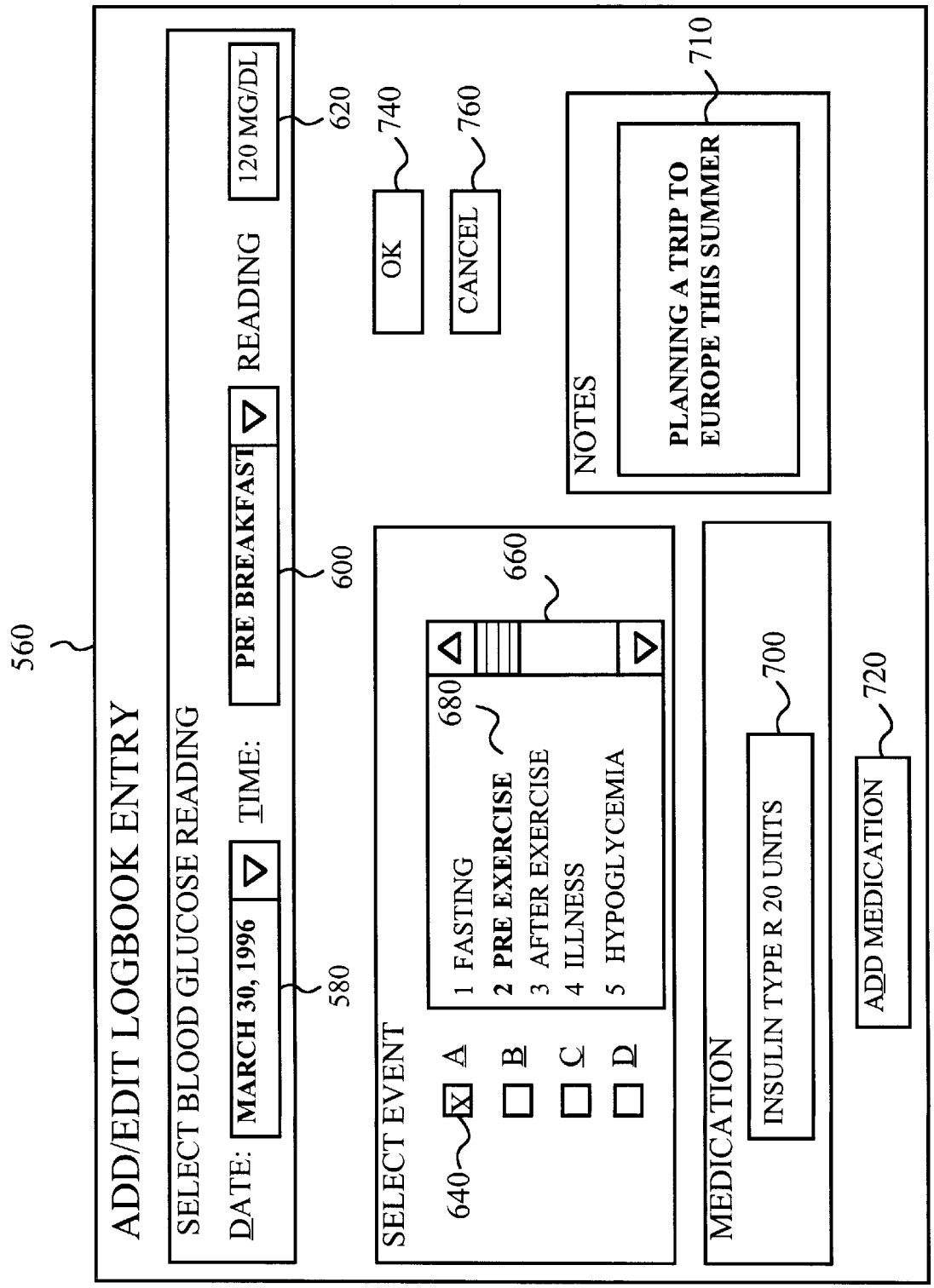

FIG. 5 shows a sample logbook entry screen 560 of logbook program 480 as it appears on patient computing device 320.

Screen 560 illustrates a typical logbook entry for a diabetic patient. Screen 560 includes a date field 580 and a time field 600 for selecting a specific blood glucose reading 620 from device measurements 540. Screen 560 further includes four radio buttons 640. Each radio button 640 is designed to display a list of events in a list box 660. List box 660 contains a selected event 680 that has been chosen by the patient as the appropriate event corresponding to blood glucose reading 620. Screen 560 also has a notes field 710 for free form entry of other information relating to the patient's treatment plan.

Figure 7:
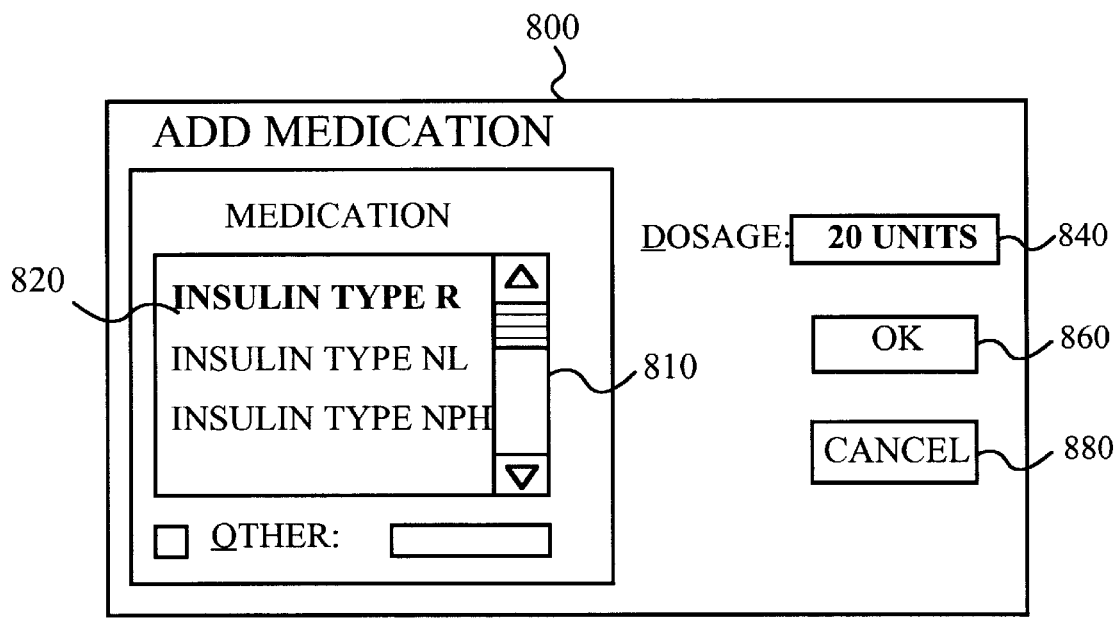
FIGS. 7–8 are sample medication entry screens appearing on the patient computing device of FIG. 4.

Screen 560 also includes an add medication button 720 for displaying an add medication screen 800, as shown in FIG. 7. Screen 800 includes a list box 810 listing diabetes medications. List box 810 contains a selected medication 820 that has been chosen by the patient. Screen 800 also includes a dosage field 840 for recording a medicine dosage. An OK button 860 and a CANCEL button 880 are for confirming and canceling, respectively, the information entered in screen 800.

Figure 8:
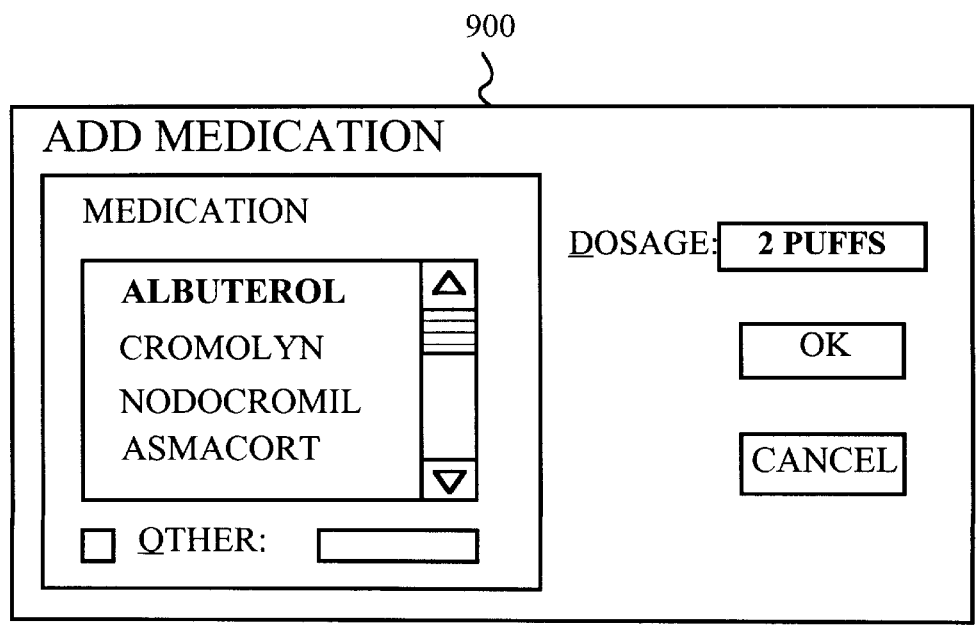

Referring again to FIG. 5, a medication field 700 shows the information entered in add medication screen 800. An OK button 740 and a CANCEL button 760 are for confirming and canceling, respectively, the logbook information entered in screen 560. FIG. 6 illustrates a sample logbook entry screen 780 for an asthmatic patient. FIG. 8 shows a sample add medication screen 900 for the asthmatic patient. The design and use of such a logbook program for entering logbook records 520 into database 400 are well known in the art.

Figure 9:
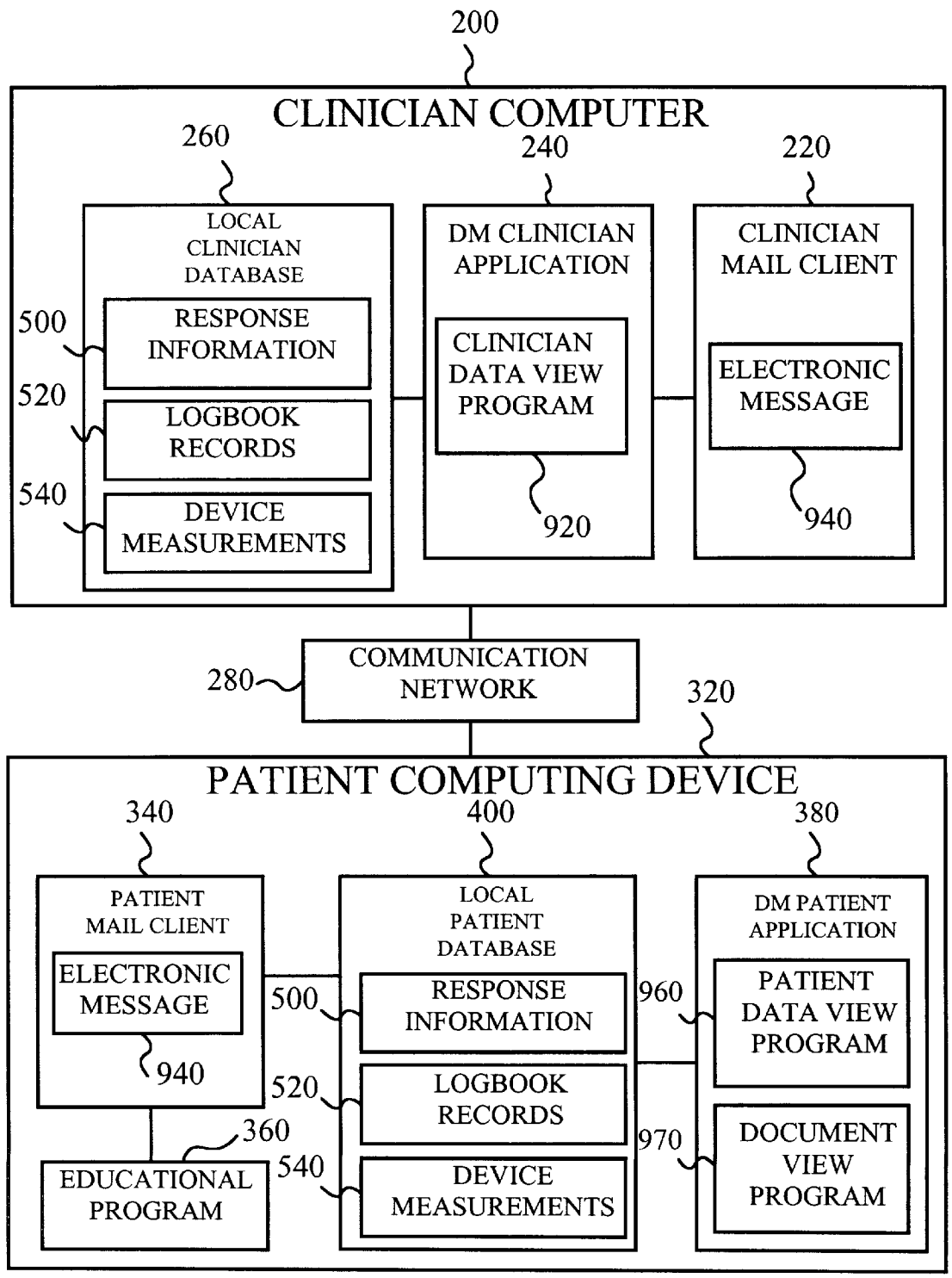
FIG. 9 is a schematic block diagram illustrating the transmitting of an electronic message in response to an analysis of the patient data of FIG. 4 according to the method of the invention.

Referring to FIG. 9, clinician data management application 240 includes a clinician data view program 920 for analyzing patient data to determine an educational need of the patient in learning to comply with his or her treatment program. Data view program 920 is capable of displaying a selected subset of device measurements 540 and logbook records 520 in graphical form.

Figure 10:
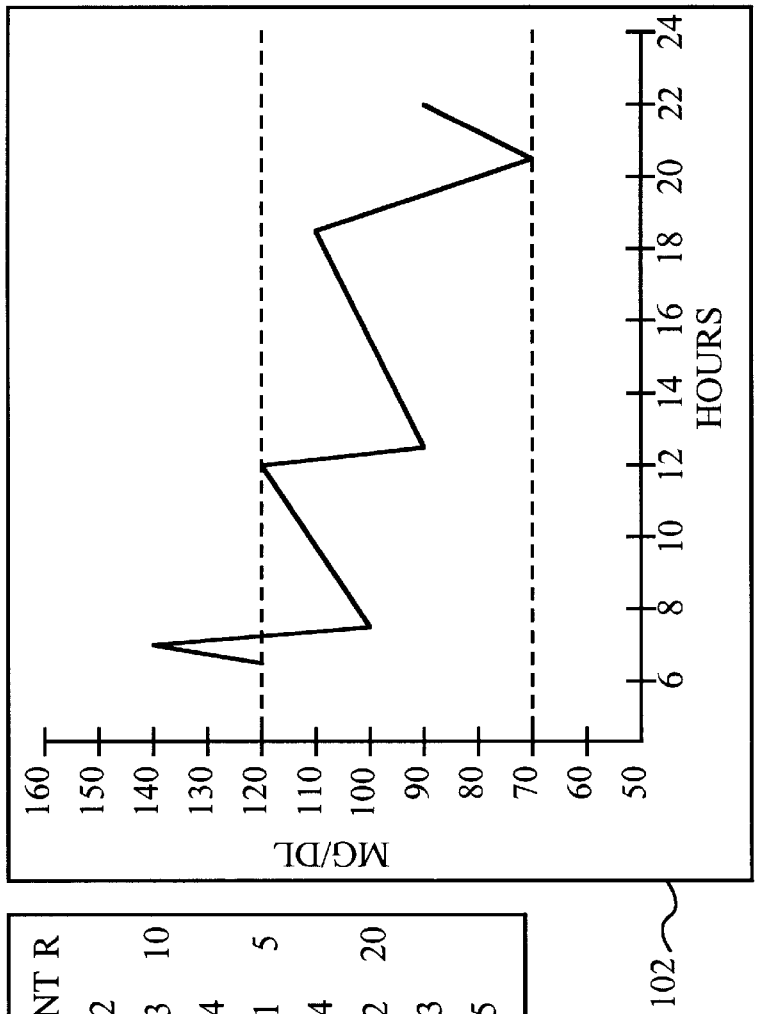
FIGS. 10–11 are sample data views appearing on the screen of a clinician computer and on the screen of the patient computing device of FIG. 4.
Figure 11:
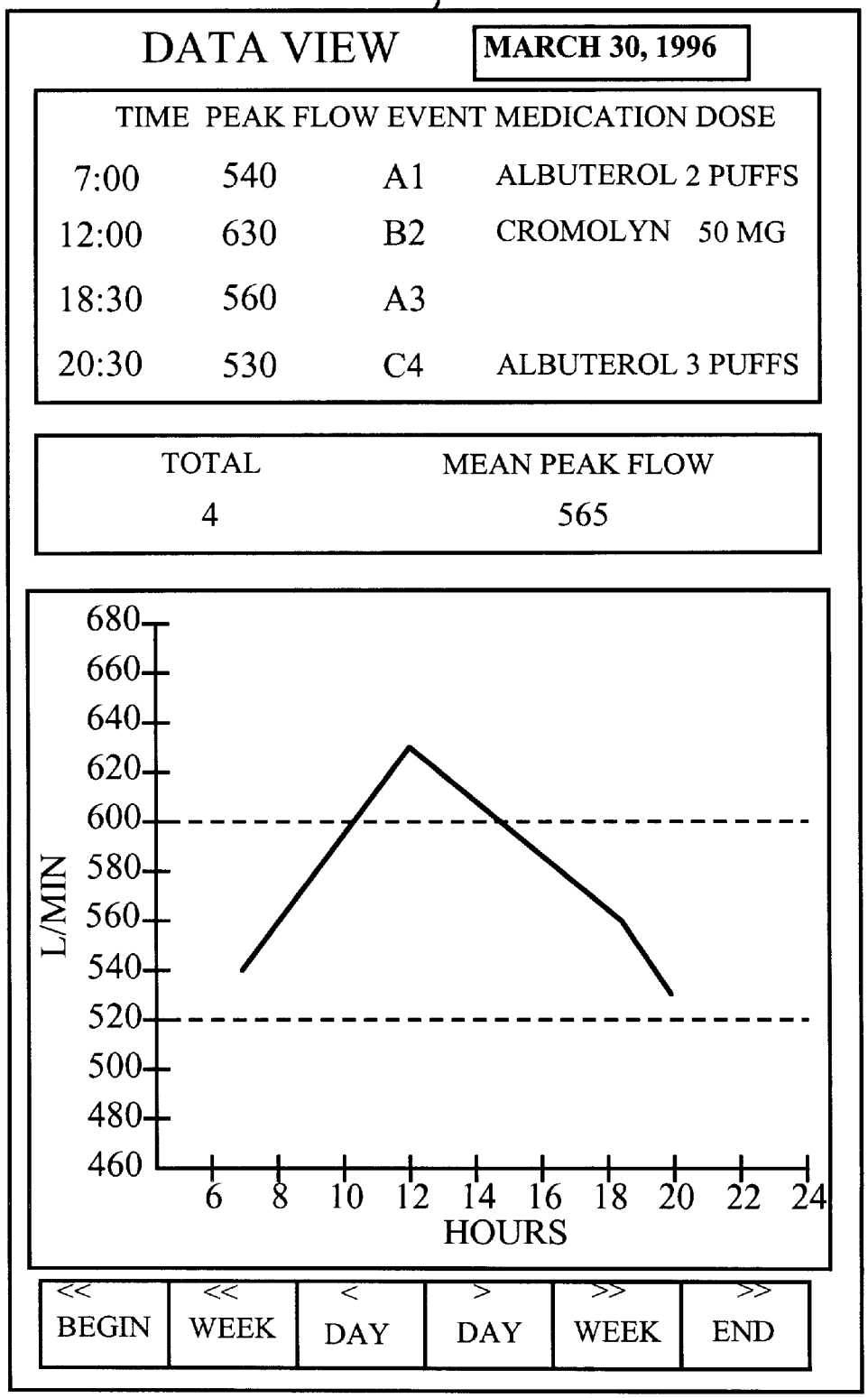

FIG. 10 shows a data view 980 produced by data view program 920 on the screen of clinician computer 200. Data view 980 is a sample data view of a diabetic patient's data. Data view 980 includes a selected subset 101 of device measurements 540 and logbook records 520 corresponding to one day in the patient's treatment plan indicated by a date field 103. Data view 980 further includes a graph 102 of selected subset 101. A set of control buttons 104 allow the clinician to scroll through different days or weeks of the patient's data to quickly view selected subsets from different days. FIG. 11 shows a sample data view 106 for an asthmatic patient's data. Specific techniques for creating a data view program to display data in this manner are well known in the art.

Referring again to FIG. 9, patient data management application 380 includes a patient data view program 960 having the same functionality as clinician data view program 920. Thus, patient data view program 960 is also capable of displaying data views 980 and 106 on patient computing device 320. Application 380 further includes a document view program 970 for displaying an educational document retrieved from on-line information service 440, as will be explained in the operation section below.

Clinician mail client 220 is of the type that allows a user to compose an electronic mail message containing an embedded pointer to a selected program installed on patient computing device 320. Mail client 220 further allows the pointer to be represented in the message as an icon. The pointer may optionally include specific data and instructions to be executed by the selected program or point to an address that has a set of instructions to be executed by the program. Patient mail client 340 is of the type that allows a user to start the selected program on patient computing device 320 by selecting the icon in the electronic mail message. A suitable electronic mail program for performing these functions is Microsoft Exchange™ commercially available from Microsoft Corporation of Redmond, Wash. The programming of an electronic mail application to perform these functions is well known in the art.

Figure 12:
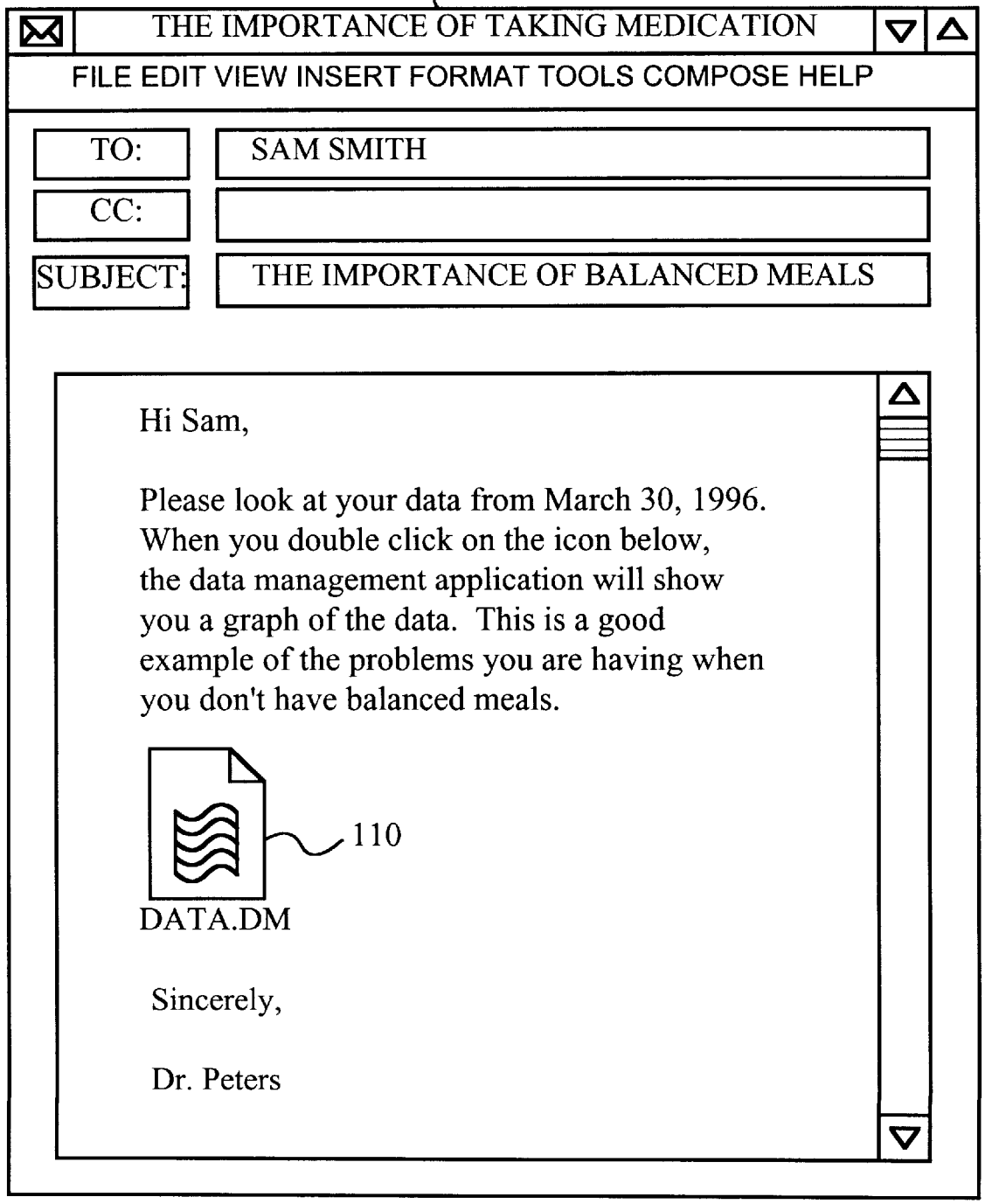
FIGS. 12–14 are sample electronic messages sent from a doctor to a patient according to the method of the invention.
Figure 13:
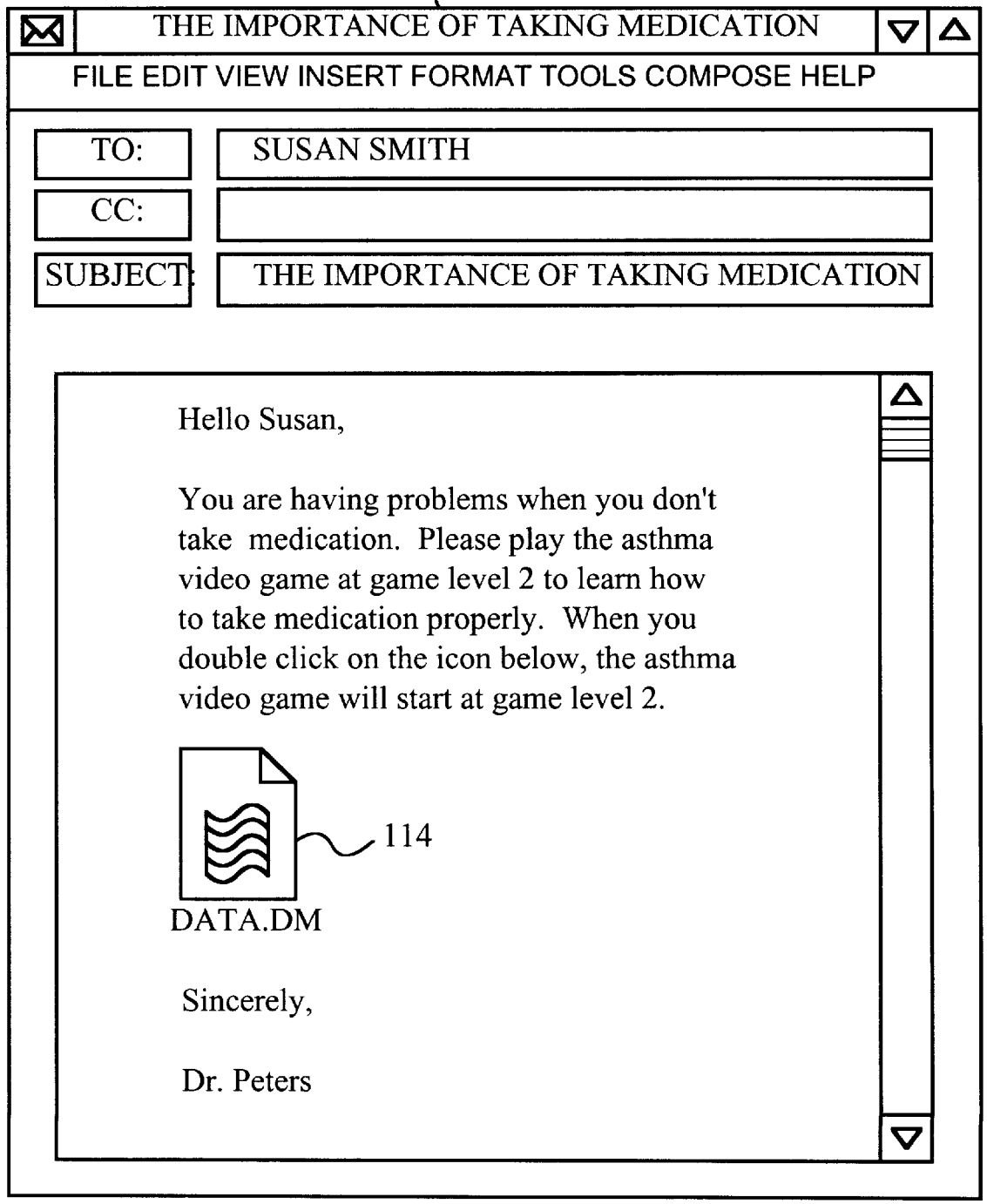
Figure 14:
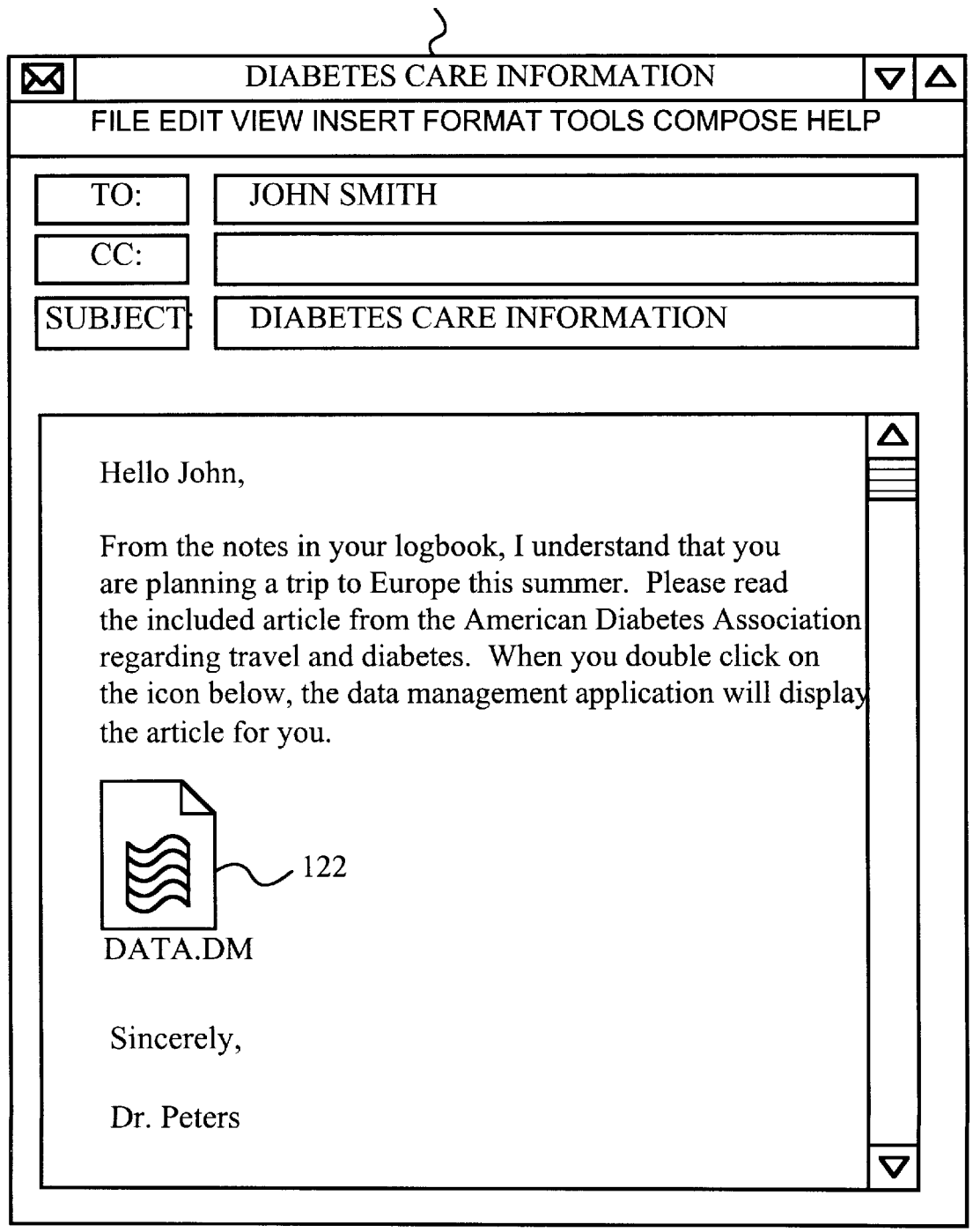

FIG. 12 illustrates a sample electronic mail message 940 in detail. Message 940 contains an icon 110 that includes an embedded pointer to patient data view program 960. Icon 110 further includes patient data from a specific date and instructions for program 960 to display the patient data in graphical form. An alternative electronic mail message 112 is illustrated in FIG. 13. Message 112 contains an icon 114 that includes an embedded pointer to educational video educational program 360. Icon 114 further includes instructions for video educational program 360 to execute Fig educational program level two. A third electronic mail message 121 is illustrated in FIG. 14. Message 121 contains an icon 122 that includes an embedded pointer to document view program 970. Icon 122 further includes an educational document retrieved from on-line information service 440 and instructions for program 970 to display the educational document.

Figure 15:
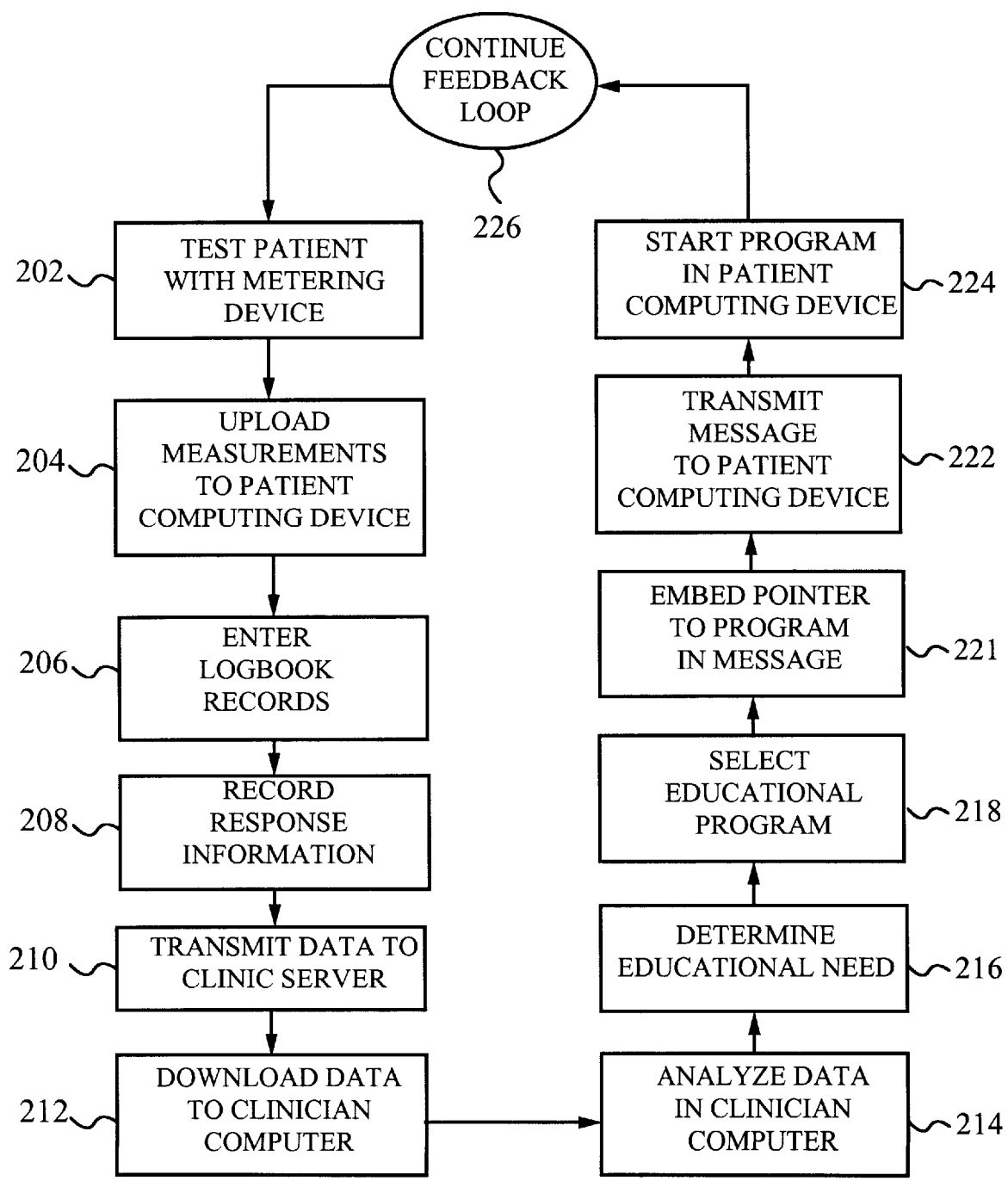
FIG. 15 is a flow chart illustrating steps included in the method of the invention.

The operation of the preferred embodiment is illustrated in FIG. 15. FIG. 15 is a flow chart showing a preferred method of using the health management system for remotely monitoring a patient and for training the patient to comply with a treatment plan for his or her health condition. In step 202, the patient is tested with metering device 420 to produce device measurements 540. Typically, the test is self-administered by the patient. Next, measurements 540 are uploaded to patient computing device 320, step 204, and stored in local patient database 400.

Once device measurements 540 are stored in database 400, the patient enters logbook records 520 into database 400 using logbook program 480, step 206. Additionally, the patient plays educational video educational program 360, entering educational program responses into patient computing device 320. As the patient plays video educational program 360, the patient's educational program responses are scored to produce knowledge score 530A, comprehension score 530B, and attitude score 530C. Knowledge score 530A, comprehension score 530B, and attitude score 530C are stored as educational program response information 500 in database 400, step 208.

Next, educational program response information 500, logbook records 520, and device measurements 540 are transmitted through communication network 280 to clinic server 120 and stored in master patient database 180, step 210. In a typical implementation, clinic 100 manages the healthcare of hundreds of patients and the data for each patient is stored in master patient database 180. A clinician at clinician computer 200 downloads patient data of a particular patient for whom he or she is responsible from master patient database 180 to local clinician database 260, step 212.

The downloaded patient data is analyzed in clinician computer 200 using clinician data view program 920, step 214. As shown in FIG. 10, data view program 980 displays on clinician computer 200 graph 102 of selected subset of data 101. The clinician also analyzes knowledge score 530A, comprehension score 530B, and attitude score 530C to assess the patient's psychological state. Based on analysis of the patient data, the clinician determines an educational need of the patient for learning to comply with a treatment program, step 216. A first example of such an educational need is illustrated in FIG. 12. As indicated in electronic mail message 940, the clinician has determined that the patient needs to learn the health consequences of failing to eat balanced meals in a diabetes treatment plan.

A second example of an educational need is illustrated in FIG. 13. As indicated in electronic mail message 112, the clinician has determined that the patient needs to learn the importance of taking medication. A third example of an educational need is illustrated in FIG. 14. As indicated in electronic mail message 121, the clinician has determined that the patient needs to learn how to treat diabetes while traveling. Of course, these are just a few examples of possible educational needs of the patient. The clinician may identify many other educational needs, such as the patient's need to learn coping skills, communication skills, and other social adjustment factors.

Once the clinician has determined the patient's educational need, he or she selects an educational program corresponding to the educational need, step 218, and embeds in an electronic message a pointer or a prompt to the educational program, step 221. The program will execute when the patient selects the pointer or reponds to the prompt. In the preferred embodiment, the educational program is selected to be either patient data view program 960, educational video educational program 360, or document view program 970 depending on the educational need determined by the clinician.

FIG. 12 shows an example of the clinician selecting data view program 960 as the educational program. The clinician embeds a pointer to program 960 in icon 110. The clinician further loads icon 110 with patient data from a specific day and instructions for program 960 to display the patient data in graphical form. FIG. 13 shows an example of the clinician selecting a educational program level of educational video educational program 360 as the educational program. The clinician embeds a pointer to the selected educational program level of video educational program 360 that has an educational content corresponding to the patient's educational need. FIG. 14 shows an example of the clinician selecting document view program 970 as the educational program. The clinician embeds a pointer to program 970 in icon 122. The clinician further loads icon 122 with an educational document retrieved from information service 440.

Next, the electronic message containing the embedded pointer is transmitted from clinician computer 200 to patient computing device 320 through mail server 140 and communication network 280, step 222. The selected educational program is then started on the patient computing device by selecting the embedded pointer in the electronic mail message, step 224, typically by clicking the icon in which the pointer is embedded with a mouse or pointing device.

As the patient works with the educational program, he or she continues the feedback loop with the clinician, step 226, by returning to step 202 and repeating the method described. With this continuous feedback loop between the patient and clinician, the clinician is able to monitor the patient's progress and effectively train the patient to comply with the treatment plan.

SUMMARY, RAMIFICATIONS, AND SCOPE

Although the above description contains many specificities, these should not be construed as limitations on the scope of the invention but merely as illustrations of the presently preferred embodiment. Many other embodiments of the invention are possible. For example, in one alternative embodiment, the clinic server is eliminated from the system so that the clinician computer exchanges information directly with the patient computing device. The clinic server is presently preferred for performing resource intensive operations, such as storing large amounts of patient data, but the clinic server is not necessary to enable the system and method of the invention. In embodiments that include the clinic, server, the clinic server need not be physically located at the clinic. The server may be located off-site and networked to the clinician computer.

Additionally, the preferred embodiment describes the use of modems for connecting the various computers in the health management system to the communication network. However, it is obvious that many other types of connections may be employed, such as ethernet connections. Specific techniques for networking computers are well known in the art.

Further, the logbook entry screens illustrated are exemplary of just one possible embodiment of the invention. In alternative embodiments, the logbook entry screens and logbook records include fields for entering and storing other health-related parameters, such as the patient's dietary intake and exercise routines. Similarly, the data views illustrated are exemplary of just one possible embodiment. Many other data views are possible, such as weekly views of the patient's data, trend graphs of the patient's data, and calendar views of the patient's logbook records.

Although the preferred embodiment describes a system and method for training patients having diabetes or asthma, the invention is not limited to patient's with these diseases. The system and method of the invention are equally effective for training patients to comply with treatment plans for other health conditions, such as cardiovascular diseases, high blood pressure, mental health conditions, addictions, or diet and exercise problems.

Therefore, the scope of the invention should be determined, not by examples given, but by the appended claims and their legal equivalents.

I claim:

1. A method for remotely monitoring a patient and for training the patient to comply with a treatment plan for a health condition, the method comprising the following steps:

a) entering in a patient computing device data relating to the health condition;

b) transmitting the data from the patient computing device to a clinician computer via a communication network;

c) analyzing the data received in the clinician computer to determine an educational need of the patient;

d) selecting in the clinician computer an educational program corresponding to the educational need;

e) transmitting an electronic message from the clinician computer to the patient computing device, wherein the electronic message contains an embedded pointer to the selected educational program; and f) starting the educational program on the patient computing device by selecting the embedded pointer in the electronic message.

2. The method of claim 1, wherein the educational program comprises an educational video program.

3. The method of claim 1, wherein the educational program comprises questions.

4. The method of claim 3, wherein patient answers to the questions are sent to the clinician computer to create and update a patient database.

5. The method of claim 1, wherein the educational program comprises a patient data view program for displaying a selected subset of the data in graphical form.

6. The method of claim 1, wherein the educational program comprises a document view program for displaying an educational document.

7. The method of claim 6, wherein the educational document is retrieved from an on-line information service connected to the communication network.

8. The method of claim 1, wherein the embedded pointer to the educational program comprises an icon.

9. The method of claim 1, wherein the data comprises measurements of a physical characteristic of the health condition and wherein the entering step comprises:

a) testing the patient with a metering device to produce the measurements; and b) uploading the measurements from the metering device to the patient computing device.

10. The method of claim 1, wherein the data comprises records of the treatment plan and wherein the records are entered in the patient computing device using a logbook program installed on the patient computing device.

11. The method of claim 1, wherein the data comprises information derived from patient responses to an educational video program played on the patient computing device and wherein the patient responses are entered by the patient while playing the educational video program.

12. The method of claim 11, wherein the information derived from the patient responses comprises a comprehension score for indicating a cognitive ability of the patient to understand the educational video program.

13. The method of claim 11, wherein the information derived from the patient responses comprises a knowledge score for indicating the patient's understanding of the treatment plan.

14. The method of claim 11, wherein the information derived from the patient responses comprises an attitude score for indicating the patient's attitude toward complying with the treatment plan.

15. The method of claim 1, wherein the data is analyzed by a clinician using a clinician data view program on the clinician computer.

16. A system for remotely monitoring a patient and for training the patient to comply with a treatment plan for a health condition, the system comprising:
   a) a patient computing device for collecting data relating to the health condition;
   b) a clinician computer having an analysis means for analyzing the data to determine an educational need of the patient, the clinician computer further having a message means for composing an electronic message containing an embedded pointer to an educational program that corresponds to the educational need; and
   c) a communication network for connecting the patient computing device to the clinician computer and for transmitting the data and the electronic message therebetween;
   wherein the patient computing device further has a means for starting the educational program when the patient selects the embedded pointer in the electronic message.

17. The system of claim 16, wherein the educational program comprises an educational video program played on the patient computing device.

18. The system of claim 16, wherein the educational program comprises a patient data view program for displaying a selected subset of the data in graphical form.

19. The system of claim 16, wherein the educational program comprises a document view program for displaying an educational document.

20. The system of claim 16, wherein the analysis means comprises a clinician data view program for displaying a selected subset of the data in graphical form.

21. The system of claim 16, wherein the embedded pointer to the educational program comprises an icon.

22. A method for remote patient monitoring and remote patient training using a computer system, the computer system comprising a clinician computer, a patient computing device having an educational program loaded thereon, and a communication network connecting the clinician computer to the patient computing device, the method comprising the following steps:
   a) entering in the patient computing device data relating to a health condition of a patient;
   b) transmitting the data from the patient computing device to the clinician computer via the communication network;
   c) analyzing the data received in the clinician computer to determine an educational need of the patient;
   d) selecting a segment of the educational program having an educational content corresponding to the educational need;
   e) transmitting an electronic message from the clinician computer to the patient computing device, wherein the electronic message contains an embedded pointer to the selected segment; and
   f) starting the educational program on the patient computing device at the selected segment by selecting the embedded pointer in the electronic message.

23. The method of claim 22, wherein the data comprises measurements of a physical characteristic of the health condition and wherein the entering step comprises:
   a) testing the patient with a metering device to produce the measurements; and
   b) uploading the measurements from the metering device to the patient computing device.

24. The method of claim 22, wherein the data comprises records of a treatment plan for the health condition and wherein the records are entered into the patient computing device using a logbook program installed on the patient computing device.

25. The method of claim 22, wherein the data comprises information derived from patient responses to the educational video program and wherein the patient responses are entered in the patient computing device by the patient while playing the educational video program.

26. The method of claim 25, wherein the information derived from the patient responses comprises a comprehension score for indicating a cognitive ability of the patient to understand the educational video program.

27. The method of claim 25, wherein the information derived from the patient responses comprises a knowledge score for indicating the patient's understanding of the treatment plan.

28. The method of claim 25, wherein the information derived from patient responses comprises an attitude score for indicating the patient's attitude toward complying with the treatment plan.

29. The method of claim 22, wherein the embedded pointer to the selected segment comprises an icon.

* * * * *

UNITED STATES PATENT AND TRADEMARK OFFICE
CERTIFICATE OF CORRECTION

PATENT NO. : 5,960,403
DATED : September 28, 1999
INVENTOR(S) : Stephen J. Brown It is certified that error appears in the above-identified patent and that said Letters Patent is hereby corrected as shown below:

Title page,
Related U.S. Application Data is amended as follows:
-- Continuation-in-part of application No. 08/481,925, Jun. 7, 1995, Pat. No. 5,899,855, which is a continuation of application No. 08/233,397, Apr. 26, 1994, now abandoned, which is a continuation-in-part of application No. 07/977,323, Nov. 17, 1992, Pat. No. 5,307,263, and a continuation-in-part of application No. 08/666,242, Jun. 20, 1996, abandoned. --

Column 7,
Line 22, the word "persona:" should be -- personal. --
Line 27, the word "with" should be -- With. --

Column 15,
Line 65, the word "Fig" should be deleted.

Signed and Sealed this

Twenty-third Day of April, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.    : 5,960,403
DATED         : September 28, 1999
INVENTOR(S)   : Stephen J. Brown It is certified that error appears in the above-identified patent and that said Letters Patent is hereby corrected as shown below:

<u>Title page,</u>
Item [63], Related U.S. Application Data, should read
-- [63] Continuation-in-part of application no. 08/481,925, Jun 7, 1995, now U.S. Patent No. 5,899,855, which is a FWC of 08/233,397, now abandoned, which is a continuation-in-part of 5,307,263, and this is a continuation-in-part of 08/666,242. --

Signed and Sealed this

Twenty-first Day of June, 2005

JON W. DUDAS
*Director of the United States Patent and Trademark Office*